United States Patent
Umentum et al.

(10) Patent No.: US 10,098,787 B2
(45) Date of Patent: Oct. 16, 2018

(54) MODULAR EYE PROTECTION

(71) Applicant: TIDI Products, LLC, Neenah, WI (US)

(72) Inventors: Katie Umentum, De Pere, WI (US); Curt Wentzel, Appleton, WI (US); Adam Poppert, Milwaukee, WI (US); Kurt J. Miller, Neenah, WI (US); Vincent E. Portelli, Oshkosh, WI (US); Rob Sweitzer, Wauwatosa, WI (US); Brad Binder, Oshkosh, WI (US); William James Evans, San Francisco, CA (US); Matt Presta, San Mateo, CA (US)

(73) Assignee: TIDI Products, LLC, Neenah, WI (US)

( * ) Notice: Subject to any disclaimer, the term of this patent is extended or adjusted under 35 U.S.C. 154(b) by 203 days.

(21) Appl. No.: 14/762,090

(22) PCT Filed: Jan. 21, 2014

(86) PCT No.: PCT/US2014/012326
§ 371 (c)(1),
(2) Date: Jul. 20, 2015

(87) PCT Pub. No.: WO2014/113791
PCT Pub. Date: Jul. 24, 2014

(65) Prior Publication Data
US 2015/0351965 A1 Dec. 10, 2015

Related U.S. Application Data

(60) Provisional application No. 61/754,670, filed on Jan. 21, 2013.

(51) Int. Cl.
*A61F 9/04* (2006.01)
*A61F 9/02* (2006.01)
(Continued)

(52) U.S. Cl.
CPC ............... *A61F 9/029* (2013.01); *A47F 1/08* (2013.01); *A61F 9/026* (2013.01); *A61F 9/027* (2013.01);
(Continued)

(58) Field of Classification Search
CPC .................................. A61F 9/028; A47F 1/08
See application file for complete search history.

(56) References Cited

U.S. PATENT DOCUMENTS 5,842,598 A * 12/1998 Tsuchida ............. B65G 59/105
221/258
7,175,270 B2 * 2/2007 Curci ...................... G02C 5/04
351/41

(Continued)

*Primary Examiner* — Timothy R Waggoner
*Assistant Examiner* — Ayodeji T Ojofeitimi
(74) *Attorney, Agent, or Firm* — Boyle Fredrickson, S.C.

(57) ABSTRACT

Modular eye protection may include a frame, temples, and a frame, which may comprise temples and a top bar. The modular eye protection may also include a modular headband with a forehead pad, lens, and elastic band. Both embodiments of the modular eye protection may be assembled with eye shield lenses or face shields lenses. Dispensing units may also dispense the various components of the modular eye protection. The modular nature, method of assembly, and dispensers allow for minimal physical contact with objects, mitigating contact with pathogens in areas such as surgical rooms where cleanliness is important. The modular eye protection may also be disposable to further prevent spreading of pathogens.

10 Claims, 13 Drawing Sheets

(51) Int. Cl.
*A47F 1/08* (2006.01)
*A61F 15/00* (2006.01)

(52) U.S. Cl.
CPC ................ *A61F 9/028* (2013.01); *A61F 9/04* (2013.01); *A61F 15/001* (2013.01)

(56) References Cited

U.S. PATENT DOCUMENTS

| | | | | |
|---|---|---|---|---|
| 8,136,697 | B2* | 3/2012 | Hackney | A47F 1/08 221/303 |
| 8,214,921 | B2* | 7/2012 | Grad | A61F 9/025 2/11 |
| 8,991,686 | B2* | 3/2015 | Schultz | B65D 83/0876 220/62 |
| 2010/0018987 | A1* | 1/2010 | Hamer | B65D 83/0454 221/25 |
| 2013/0014316 | A1* | 1/2013 | Castro | A41D 13/1184 2/424 |
| 2014/0318084 | A1* | 10/2014 | Schultz | B65D 5/42 53/456 |
| 2014/0319205 | A1* | 10/2014 | Schultz | B65D 5/725 229/122.1 |

* cited by examiner

MODULAR EYE PROTECTION

CROSS-REFERENCES TO RELATED APPLICATIONS

This application is a National Stage Entry of International Patent Application No. PCT/US2014/012326 filed on Jan. 21, 2014 which claims a benefit of priority under 35 USC § 119 to U.S. Provisional Patent Application No. 61/754,670, filed Jan. 21, 2013, the entire contents of both which are hereby expressly incorporated by reference into the present application.

BACKGROUND OF THE INVENTION

1. Field of the Invention

The present invention relates to the field of protective eyewear. In particular, the invention is related to disposable, modular eye protection that is easy to assemble in a modular fashion.

2. Discussion of the Related Art

U.S. Pat. No. 5,440,760 discloses a disposable face shield. The face shield protects the wearer against airborne particles and droplets that potentially contain pathogens. The face shield includes a plastic shield with a cord attached to a crescent shaped foam member for securing the shield about the wearer's face. The foam member is designed to conform to the wearer's forehead.

One particular problem of the above-mentioned face shield is that when a plurality of face shields is stored they occupy a great deal storage space. Furthermore, should the wearer desire an eye shield in addition to a face shield, or instead of a face shield, even more storage space must be used. The pre-assembly of face shields or of eye shields also adds to the cost of the protective wear.

An added disadvantage is the dispensing process of a typical face shield or eye shield. Normally, these types of products are stored in boxes or bags, which are stored in cabinetry. In a healthcare facility, hand sanitation is very critical to mitigate the spread of pathogens. Thus, the handling of packaging cabinet doorknobs, and drawers introduces opportunities for a person's hands to contact a pathogen.

Therefore, what is needed is a convenient way to store and dispense eye protection such as face shields and eye shields. What is also needed is a storage and dispensing device that minimizes contact with a person's hands on any objects. What is further needed is an eye protection design that can either be formed into eye shields or a face shield using common parts.

SUMMARY AND OBJECTS OF THE INVENTION

Modular eye protection is hereby disclosed with a frame including arms extending from the sides of the frame, for example, temples. The frame also includes a top bar, and a detachable nose bridge. The frame is configured to attach to a lens with an interference fit. A lens preferably attaches to the frame with a male and a female component that are retained together with an interference fit. The modular eye protection is also configured to be disposable following a single use. The nose bridge provides a space between the lens and the person's face so the lens is not in contact with the person's face. This provides a level of ventilation and prevents the lens from fogging up during use.

Additionally, the frame is configured to receive both a face shield lens to cover a majority of a person's face and an eye shield lens to cover a person's eyes. This makes the frame modular and it can be used to construct an eye shield or a face shield, depending on the wearer's needs.

In order to minimize the storage space necessary to store the modular eye protection, a dispenser is configured to conveniently store and dispense a plurality of frames, detachable nose bridges, and lenses. This lessens the amount of hand contact a person needs to make with cabinet doors, knobs, and packaging thus helping keep the hands more sanitary. This is especially important in healthcare environments.

The dispenser preferably includes a frame-dispensing portion with a vertical, unobstructed dispensing column. A dispensing opening is at a bottom portion of the column. The dispenser is preferably further configured to receive a cartridge of a plurality of frames and dispense a single frame at a time. Each frame may be dispensed with a dispensing means that is a spring-loaded device or an electronically actuated device. Preferably, the dispensing means also includes an unobstructed column that uses gravity to advance a frame after one is removed. The dispenser may further include a lens-dispensing portion attached to the frame-dispensing portion with an eye shield lens and a face shield lens-dispensing portion. The face shield lens-dispensing portion includes a storage compartment configured to store a plurality of face shield lenses and a slider configured to advance a new face shield lens following a dispensing of a face shield. The eye shield lens-dispensing portion includes a storage compartment configured to store a plurality of eye shield lenses, and a slider configured to advance a new eye shield lens following a dispensing of an eye shield lens. An access panel opens and closes allowing access to a storage compartment of the eye shield lens-dispensing portion and the face shield lens-dispensing portion, in order to allow personnel to refill any of the various parts, as they are dispensed. Stored lenses are kept clean and hygienic in the covered storage compartment. A large quantity of stored lenses (1000 or more) is made possible by various methods including perforated roll, or z-fold, or stacking. The dispenser when advancing the lenses will separate the perforations if in a roll or z-fold. If lenses are stacked, the dispenser will control the dispensing of lenses in a way to permit only one lens to be advanced using friction rollers or other mechanisms. The large supply of bulk frames and lenses will enable less frequent resupply and increase compliance due to reliable availability of the protective eyewear. While each lens is dispensed without any packaging in one embodiment, in another embodiment, a bagged dispensing portion may be connected to the lens-dispensing portion and configured to dispense a plurality of individually bagged eye shield lenses, individually bagged face shield lenses, or individually bagged masks. The dispensing system may also include a reprocessing bin for storage of reusable frames to be disinfected or sterilized, or a similar disposal compartment for lenses or frames to be discarded.

The dispenser will allow for a kanban-style resupply system, giving an externally visible indication of the need to refill any compartment. The compartments will allow sufficient space for the amount of units in a standard refill cartridge plus the remaining few units that triggered the resupply visual notification. The size and shape of the frame reprocessing bin will match the dispensing compartment, such that a matching quantity of inventory rotation between the usage point and sterile processing is possible.

The dispenser will allow for a transparent document holder on the front surface, such that usage guidelines and educational messages can be placed by users.

Electronic versions of inventory monitoring and resupply notification are envisioned, with the possibility of resupply messages sent to central supply via wireless or LAN. The transparent document holder would be replaced by an optional programmable LCD color display in the electronic version.

The modular eye protection may also include a first plurality of openings in the frame with a second plurality of channels extending through the frame. Each lens may include a second plurality of openings in a top portion of the lens with a second plurality of channels extending through the lens. The first plurality of channels may be in fluid communication with the second plurality of channels through the first and second plurality of openings, forming a venting system when the frame is attached to the lens. The venting system may allow air to flow from in front of the modular eye protection to behind the frame through the first and second plurality of channels. In order to prevent liquid from contacting a wearer's face, a liquid trap in each channel in the lens may be configured to trap liquid entering the respective channel and prevent the liquid from entering a space behind the lens. Additionally, when forming a face shield, the modular eye protection may touch a person's cheeks on both sides of the face allowing it to wrap around the wearer's face.

The eye protection may also be assembled in a unique manner. This includes actuating a slider either manually or electronically on a dispenser to advance a lens from a lens dispenser. A frame may then be removed from a frame-dispensing portion that is attached to the lens-dispensing portion. The frame may then be attached to the lens by pushing the frame into the lens while the lens is still contained within the lens-dispensing portion, forming one of an eye shield and a face shield. Either an eye shield or a face shield may then be removed from the lens-dispensing portion, depending on which parts were selected.

Another method of assembling the modular eye protection may include connecting a frame to a lens by pushing the frame against the lens, while the lens is still stored in a dispenser. The frame may then be pivoted to an angle generally 90 degrees to the lens, while the lens is still stored in the dispenser. The lens may then be removed from the dispenser by pulling the frame away from the dispenser maintaining the frame at 90 degrees to the lens. A first and second end of the lens may then be attached to receiving holes in each of the first and second temples of the frame with a push-to-connect attachment.

One type of dispenser for the modular eye protection may include an enclosure containing a face shield lens-dispensing compartment and an eye shield lens-dispensing compartment. A hinged panel on a side of the enclosure may allow access to a cavity within the face shield lens-dispensing compartment and access to a cavity within the eye shield lens-dispensing compartment. Each cavity may store a plurality of face shield lenses and eye shield lenses, respectively. An opening in the eye shield lens-dispensing compartment may dispense a single eye shield lens at a time while an opening in the face shield lens-dispensing compartment may dispense a single face shield lens at a time.

Furthermore, a mask-dispensing compartment may be connected to the enclosure. An opening in the mask-dispensing compartment may dispense a single mask at a time. The hinged panel on the side of the enclosure may also allow access to a cavity within the mask-dispensing compartment for storing a plurality of masks.

Another embodiment of the invention may include a modular head band. The head band may include an elastic band configured to wrap around a head of an individual. A forehead pad may attach to the elastic band and be constructed, preferably, of a polyester foam. The forehead pad may also be constructed with a plurality of channels extending longitudinally through the forehead pad. Each channel may include an opening on each end of the forehead pad. The channels may also allow an air flow within the respective channels. In order to attach a lens to the forehead pad, the pad may include a first reception slot that receives and retains a lens. A second reception slot may be included to receive and retain the elastic band. The lens may be either a face shield to cover a majority of a person's face or an eye shield to cover a person's eyes.

The forehead pad may be selected by a wearer from a plurality of forehead pads, each having different thicknesses. The thickness is dependent on which variant the user selects; for eyeshield configuration the lens does not have to clear the nose and a thinner foam pad is sufficient. The thicker pad is selected when mated to a full face shield to achieve the stand-off required to clear the nose. The lens, of either an eye shield or a face shield, may include a printed area on an upper portion of the lens in contact with the first reception slot for producing an anti-glare effect. Optionally, a user definable printed section on the elastic band may display a logo, a message, or a picture. For example, the elastic band may display a printed sports team, entertainer, or school.

The modular head band may be dispensed by a dispenser that includes a first storage vessel with a first cavity and a plurality of forehead pads. A first opening on a lower portion of the first storage vessel may dispense a single forehead pad at a time. A second storage vessel may be attached to the first storage vessel and include a second cavity and a plurality of elastic bands. The second storage vessel may also include a second opening on an upper portion for dispensing a single elastic band at a time. Similar to drawing tissues from a tissue box, each elastic band may be connected to one another and removal of a single elastic band from the second opening detaches the single elastic band from the plurality of elastic bands within the second cavity.

The modular head band may be assembled by removing a forehead pad from an opening on a lower portion of a container. A lens may be fastened to a first reception slot in the forehead pad by inserting the lens into the first reception slot. An elastic band may be fastened to a second reception slot in the forehead pad by inserting the elastic band into the second reception slot. Additionally, multiple pre-assembled modular headbands may be stored by vertically stacking a plurality of pre-assembled modular head bands in a container and assigning a common Stock Keeping Unit (SKU) to the pre-assembled modular headband.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1A:
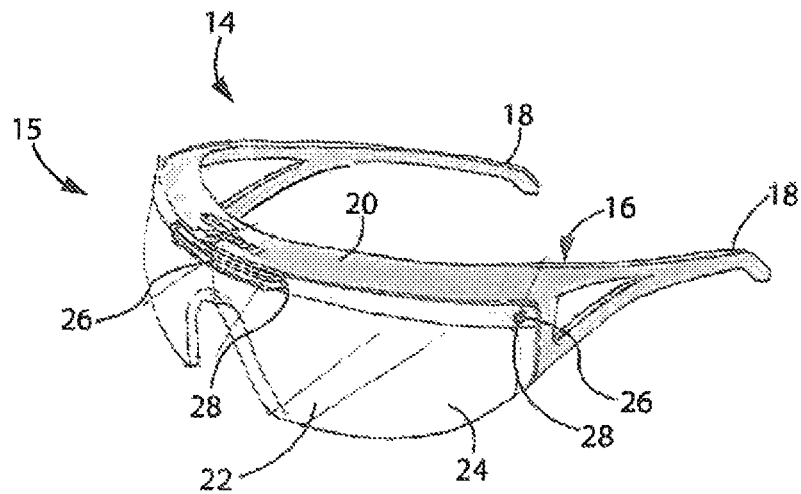
FIG. 1A illustrates a perspective view of modular eye protection according to a first embodiment of the invention.

In describing the preferred embodiment of the invention, which is illustrated in the drawings, specific terminology will be resorted to for the sake of clarity. However, it is not intended that the invention be limited to the specific terms so selected and it is to be understood that each specific term includes all technical equivalents, which operate in a similar manner to accomplish a similar purpose. For example, the words "connected," "attached," or terms similar thereto are often used. They are not limited to direct connection but include connection through other elements where such connection is recognized as being equivalent by those skilled in the art.

DETAILED DESCRIPTION OF PREFERRED EMBODIMENTS

The present invention and the various features and advantageous details thereof are explained more fully with reference to the non-limiting embodiments described in detail in the following description.

A series of modular eyewear, storage devices for said eyewear, and an assembly method of the same is hereby disclosed. Beginning with FIG. 1A, fully-assembled modular eye protection 14 is shown forming an eye shield 15. The eye shield 15 is constructed out of two basic elements, the frame 16 and a lens 22. The frame 16 includes a top bar 20 and temples 18 on each end of the top bar 20. In this instance, the lens 22 is in the form of an eye shield lens 24, thus forming an eye shield 15. As shown and described in other FIGS., the lens 22 may include a plurality of shapes. The manner in which the lens 22 attaches to the frame 16 is preferably kept constant in order to provide a modularity that allows one to assemble different modular eye protection 14 for different purposes while using similar components, such as the frame 16. Preferably, the lens 22 attaches to the frame 16 with a plurality of male components 26 extending from the frame 16 attaching to a plurality of female components 28 on an upper portion of the lens 22. The male component 26 and female component 28 may include a variety of different fasteners. Preferably, the fasteners do not require any tools and may be joined together with minimal effort. The preferred method of joining the male component 26 and the female component 28 includes the male component 26 extending from the frame 16 and passing through the female component 28 on the lens 22 in an interference fit, thus allowing friction to retain the two components together. Additionally, while the frame 16 is shown with temples 18 rigidly attached to the top bar 20, the attachment may include hinges so as to allow articulation of the temples 18 with respect to the frame 16. The frame 16 may also be constructed out of a rigid plastic material; however, it may also be a flexible material so as to allow the frame 16 to conform to a variety of different shapes.

Figure 1B:
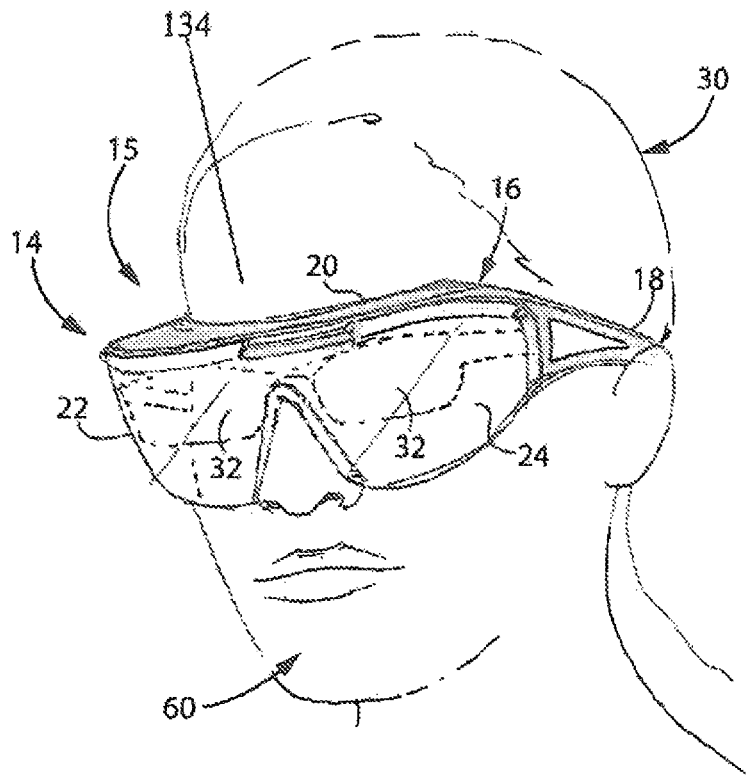
FIG. 1B illustrates a perspective view of the modular eye protection of FIG. 1 being worn by a person.

FIG. 1B shows the eye shield 15 being worn by a person 30. The lens 22 protects the eyes 32 in front of the lens 22, from the periphery of the lens 22, and from a lower portion of the lens 22. Due to the shape of the top bar 20, foreign objects are prevented from contacting the eye 32 from above the eye shield 15. The frame 16 and the top bar 20 remain in contact on all portions of the forehead 134 of the person 30. The lens 22 may be of any shape and preferably in this embodiment in the shape of an eye shield lens 24. The eye shield lens 24 may also extend down the face 60 of the person 32 to protect more than just the eyes 32.

Figure 2:
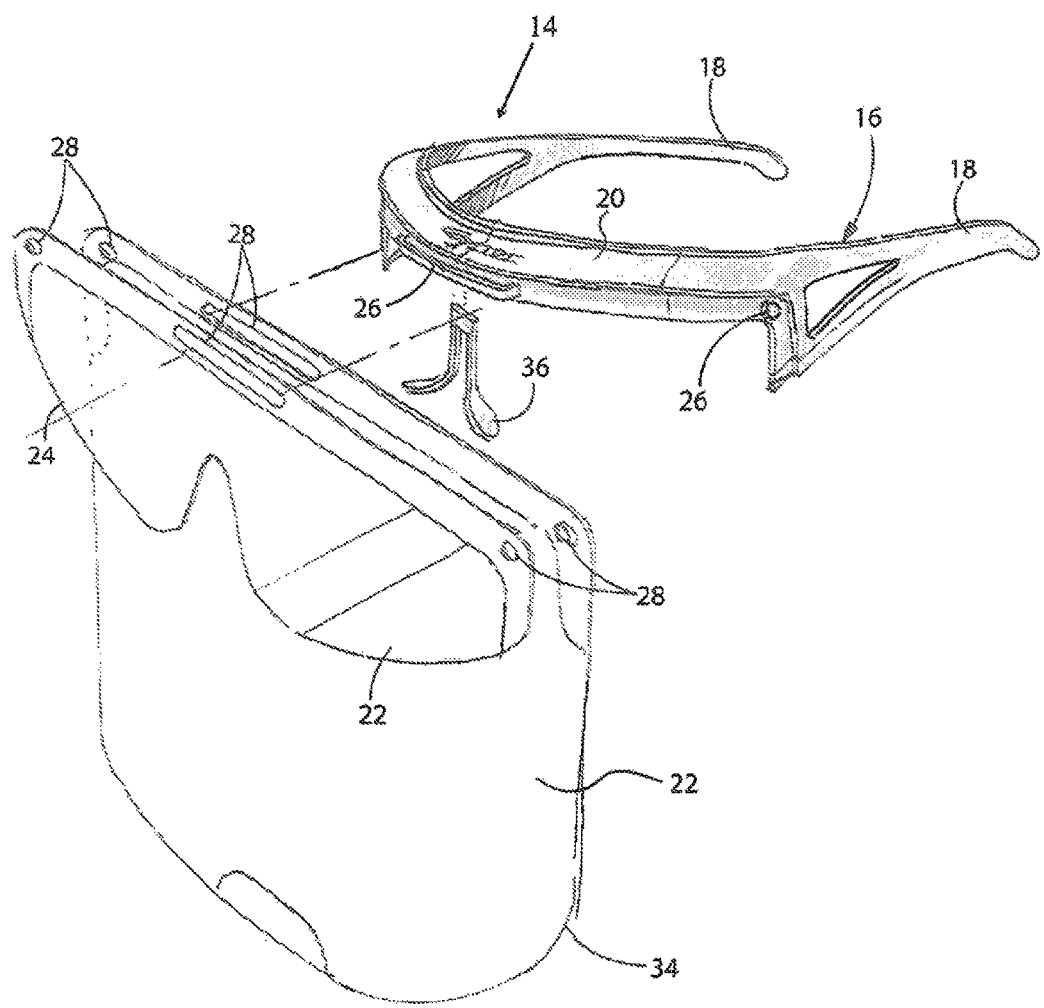
FIG. 2 illustrates an exploded view of modular eye protection according to another embodiment of the invention.

Moving on to FIG. 2, the modular eye protection 14 is shown with a variety of different components that may be attached to the frame 16. For example, the lens 22 may be either an eye shield lens 24, as shown in FIGS. 1A and 1B, or it may also include a face shield lens 34. The male components 26 on the frame are more easily seen in FIG. 2. In the center of the top bar 20, the male component 26 may include a projection extending along at least part of the length of the top bar 20. Each lens 22, whether the eye shield lens 24 or the face shield lens 34, includes female components 28 that fit with the male components 26 of the frame 16. This allows assembly of different modular eye protection 14 with the common frame 16. Additionally, the nose bridge 36 may be attached to the frame 16 to provide added support to the frame 16 and prevent movement while being worn.

Figure 3:
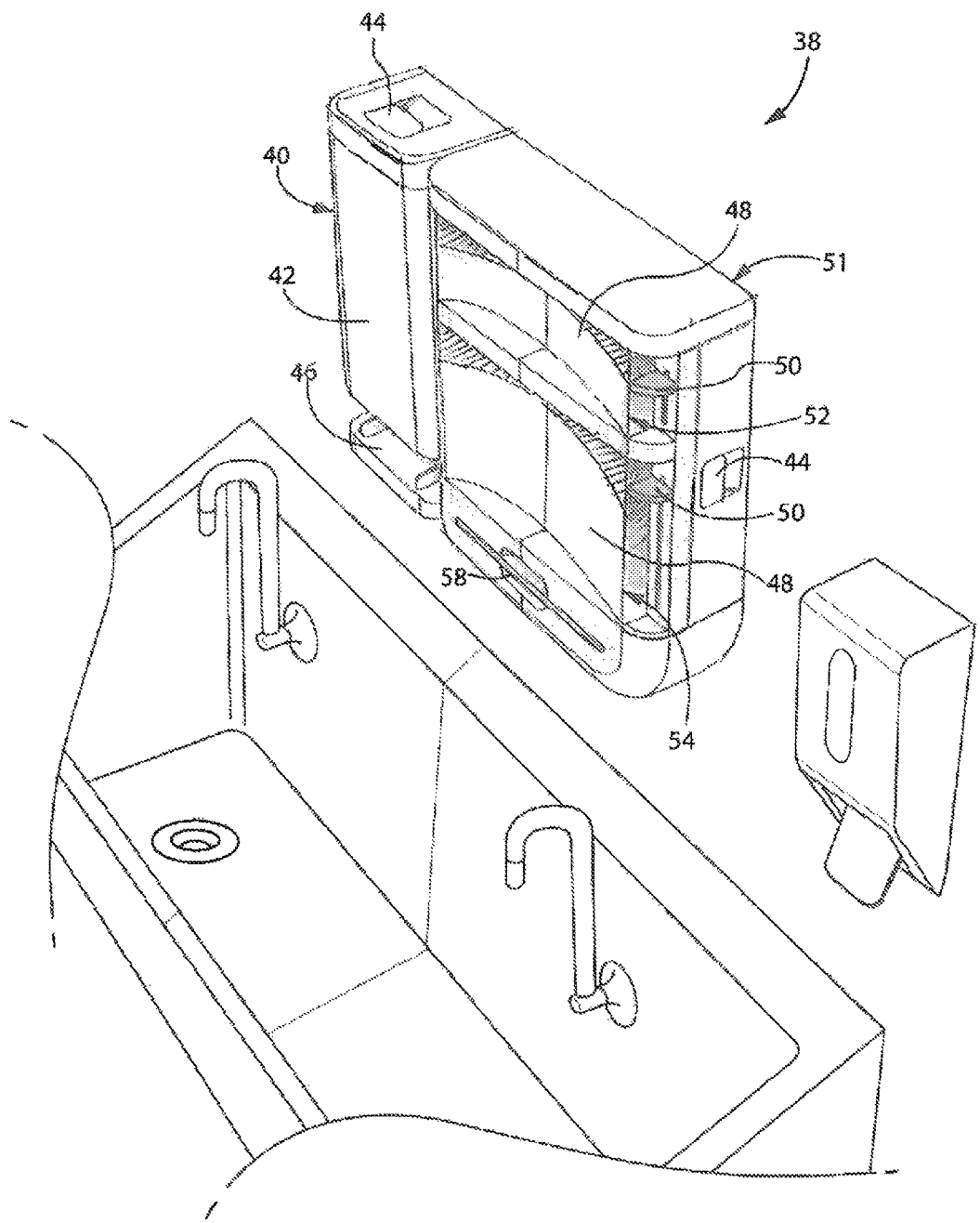
FIG. 3 illustrates a perspective view of a dispenser for modular eye protection according to another embodiment of the invention.

As shown in FIG. 3, a dispenser 38 facilitating modular construction of the modular eye protection 14 may be used. The dispenser 38 preferably includes a frame-dispensing portion 40 including a column 42 with a dispensing opening 46 on a lower portion of the column 42. An access panel 44 on an upper portion of the column 42 allows access to the interior of the column 42 for storage of the plurality of frames 16. While the frame-dispensing portion 40 may include a spring-loaded mechanism, an electronically-controlled mechanism, or any other type of device to deliver frames 16 to the dispensing opening 46, preferably the column 42 is unobstructed, and gravity powers the frame-dispensing portion 40 allowing a frame 16 to fall to the dispensing opening 46. As a frame is removed from the dispensing opening 46, gravity allows another frame 16 to fall to the dispensing opening 46 from within the column 42. Adjacent to the frame-dispensing portion 40 is a lens-dispensing portion 51. The lens-dispensing portion 51 may dispense both an eye shield lens 24 and a face shield lens 34. An eye shield lens-dispensing portion 52 may dispense eye shield lenses 24 while the face shield lens-dispensing portion 54 may dispense face shield lenses 34.

A storage compartment 48 is included in both the eye shield lens-dispensing portion 52 and the face shield lens-dispensing portion 54. The storage compartments 48 may store a plurality of eye shield lenses 24 and face shield lenses 34. A common axis panel 44 on the lens-dispensing portion 51 allows access to the storage compartments 48 of both the eye shield lens-dispensing portion 52 and the face shield lens-dispensing portion 54. While any method may be used to advance a new lens 22 in the lens-dispensing portion 51, preferably a slider 50 is included in each one of the eye shield-dispensing portion 52 and the face shield lens-dispensing portion 54. When the respective slider 50 is actuated, a lens 22 may be advanced in either the eye shield lens-dispensing portion 52 or the face shield lens-dispensing portion 54, depending on which slider 50 was actuated. Again, the slider 50 does not need to be a manually-activated device. The slider 50 may include an electronic pushbutton, a voice-actuated mechanism, or a proximity/motion sensor to detect the movement of an object, such as a hand requesting a lens 22. Such a hands-free device would mitigate the spreading of pathogens. Additionally, a bagged-dispensing portion 58 may dispense a face shield lens 34, and eye shield lens 24, a surgical mask or any other device in an individually wrapped bag.

Figure 4A:
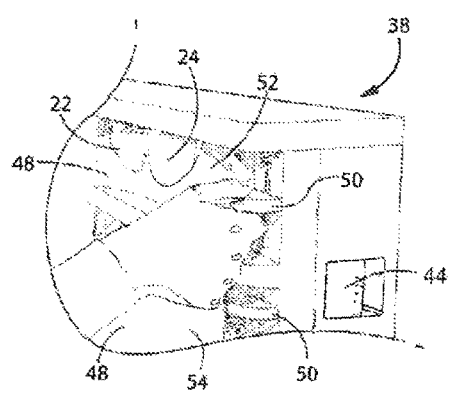
FIG. 4A illustrates a perspective view of the use of the dispenser according to FIG. 3.
Figure 4B:
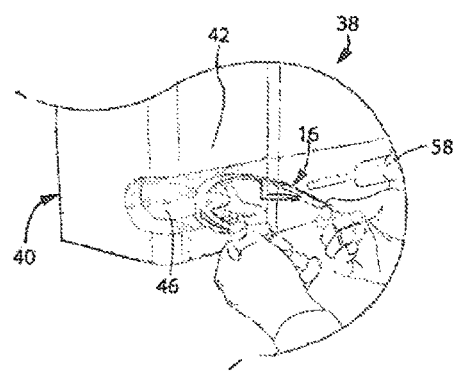
FIG. 4B illustrates a perspective view of the use of the dispenser according to FIG. 3.
Figure 4C:
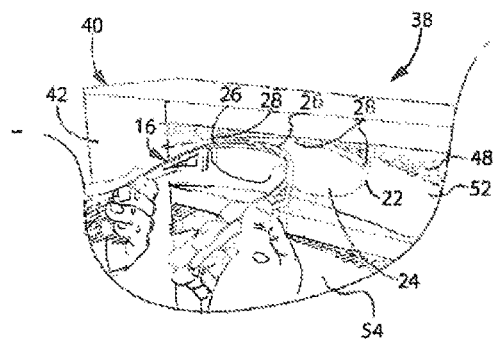
FIG. 4C illustrates a perspective view of the use of the dispenser according to FIG. 3.
Figure 4D:
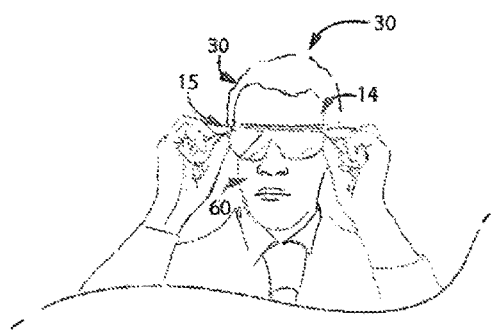
FIG. 4D illustrates a perspective view of the modular eye protection assembled in FIGS. 4A-4C being worn by a person.

FIGS. 4A, 4B, 4C, and 4D illustrate a typical example of the dispenser 38 being used. Beginning with FIG. 4A, an eye shield lens 24 may be advanced from the eye shield lens-dispensing portion 52 by actuating a slider 50 proximate to the eye shield lens-dispensing portion 52. This action causes a lens 22 to be delivered from the storage compartment 48. Similarly, activating the slider 50 proximate to the face shield lens-dispensing portion 54 advances a face shield lens 34 from the storage compartment 48 of the face shield lens-dispensing portion 54. Moving to FIG. 4B, a frame 16 may be taken from the column 42 of the dispensing opening 46 in the frame-dispensing portion 40. In order to prevent unnecessary touching of a lens 22, FIG. 4C illustrates how a lens 22 may be attached to a frame 16. The frame 16 may be physically pushed against the lens 22 allowing the female components 28 of the lens 22 to interlock with a male component 26 of the frame 16 with an interference fit. This may be done while the lens 22 is still within the respective dispensing portion. For example, if it is desired to construct an eye shield 15, one would actuate the slider 50 proximate the eye shield lens-dispensing portion 52 and press a frame 16 against the eye shield lens 24. If one were to construct a face shield 62, as shown in FIG. 5B, one would advance a face shield lens 34 from the face shield lens-dispensing portion 54 by actuating a slider 50 proximate the face shield lens-dispensing portion 54 and press a frame 16 against the face shield lens 34 allowing the female components 28 of the face shield lens 34 to interlock with a male components 26 of the frame 16 while the face shield lens 34 is still within the face shield lens-dispensing portion 54. FIG. 4D illustrates an assembled example of the modular eye protection 14, in this case an eye shield 15, which is worn on the face 60 of a person 30. The dispenser 38 allows construction of modular eye protection 14 by only touching a slider 15 and the frame 16, as discussed above.

Figure 5A:
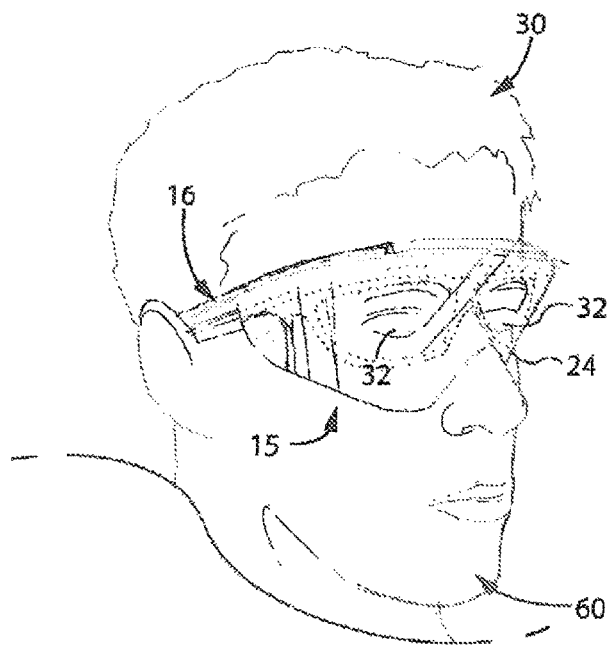
FIG. 5A illustrates a perspective view of another embodiment of modular eye protection being worn by a person.
Figure 5B:
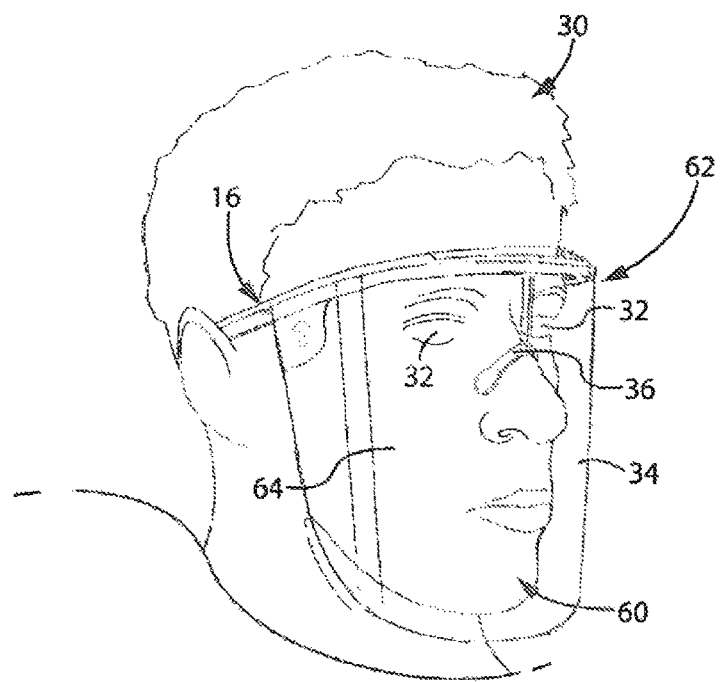
FIG. 5B illustrates a perspective view of another embodiment of modular eye protection being worn by a person.

Transitioning to FIGS. 5A and 5B, a person 30 is shown wearing a frame 16 that has been attached to either an eye shield lens 24 to form an eye shield 15, or a frame 16 to face shield lens 54 to form a face shield 62. In the example shown in FIG. 5A, an eye shield 15 is shown wherein the eye shield lens may protect more than just the eyes 32 of the person 30. The eye shield lens may extend down past the eyes 32 protect a greater area. As shown in FIG. 5B, the face shield lens 34 may include a nose bridge 36 that is attached directly to the face shield lens 34 allowing the face shield to extend a distance away from the face 60 of the person 30. This distance allows for more ventilation and prevents the face shield lens from fogging up due to the water vapor in the person's breath. The face shield lens 34 may curve around the face 60 and contact the cheeks 64 of the person 30 to add further protection against foreign objects from contacting the face 60.

Figure 6:
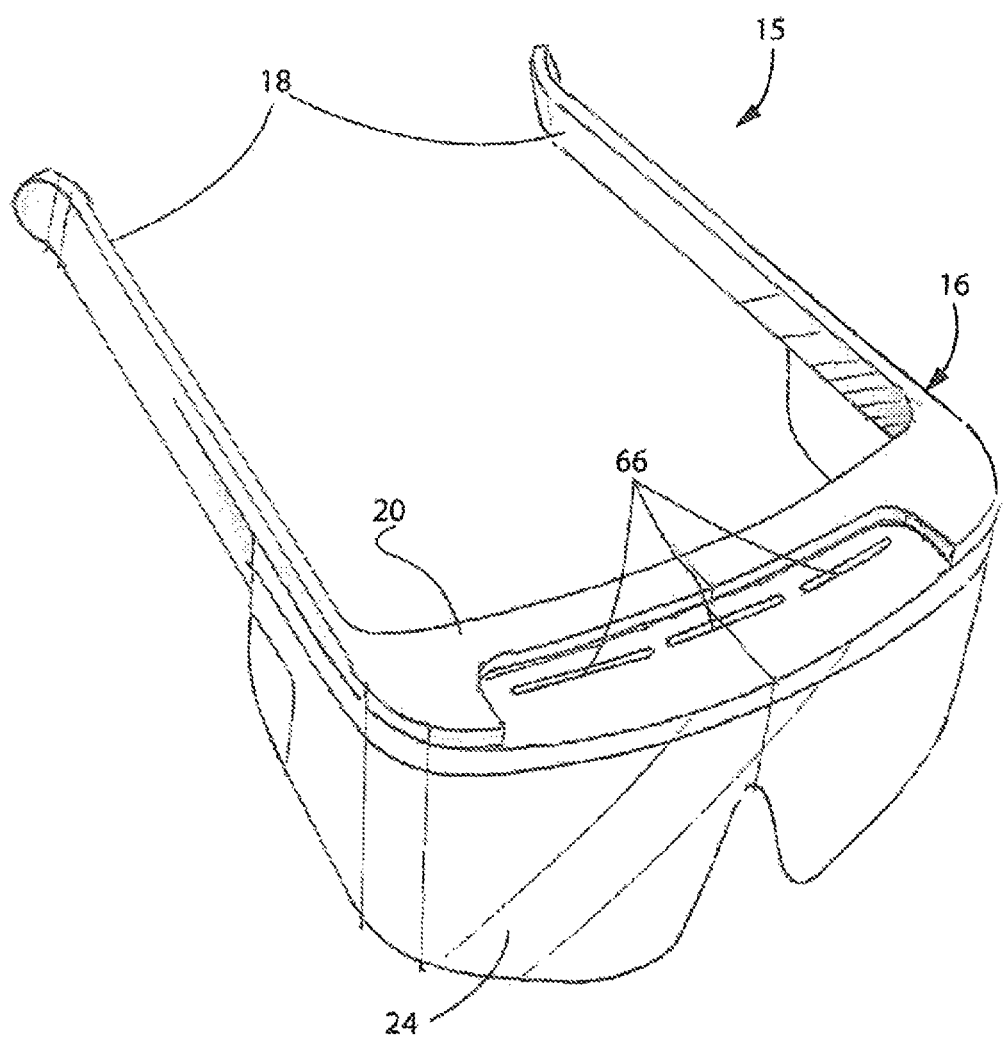
FIG. 6 illustrates a perspective view of modular eye protection according to another embodiment of the invention.
Figure 7A:
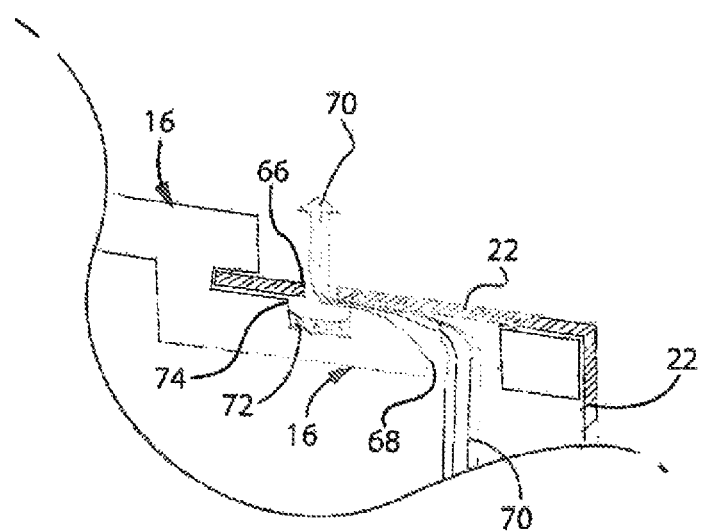
FIG. 7A illustrates a partial perspective view of modular eye protection according to another embodiment of the invention.
Figure 7B:
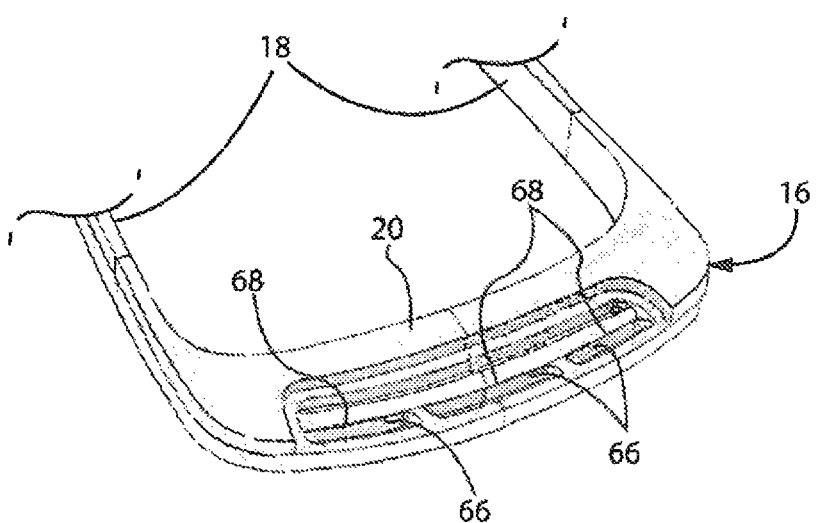
FIG. 7B illustrates a partial perspective view of modular eye protection according to another embodiment of the invention.

Another way to mitigate the fogging of any lens 22 is shown in FIG. 6. In this example, the frame 16 is constructed to build an eye shield 15 with an eye shield lens 24. A plurality of openings 66 in the top bar 20 of the frame 16 provide added ventilation to the eye shield lens 24. This ventilation is further shown in FIGS. 7A and 7B. In FIG. 7A, the opening 66 is shown to communicate with a channel 68 between a lens 22 and the frame 16. This channel 68 allows an air flow 70 between the face 60 of a person 30, as shown in FIG. 5B, and an area in front of the lens 22. The channel 68 may include a liquid trap 74 in the form of a recess in the frame 16. The liquid trap 74 prevents liquid 72 from entering the opening 66 and contacting the eyes 32 or the face 60 of a person 30. The liquid trap 74 traps and stores the liquid 72, preventing it from traveling down the channel 68. The liquid trap 74 may also collect solids, foreign objects, or any other object. A similar channel 68 and liquid trap 74, as shown in FIG. 7A, may also be included in other parts of the frame 16, as shown in FIG. 7B. The frame 16 may include multiple channels 68 and multiple openings 66 on the top bar 20. Each of the channels 68 may also include a similar liquid trap 74 and function as described above with respect to FIG. 7A.

Figure 8:
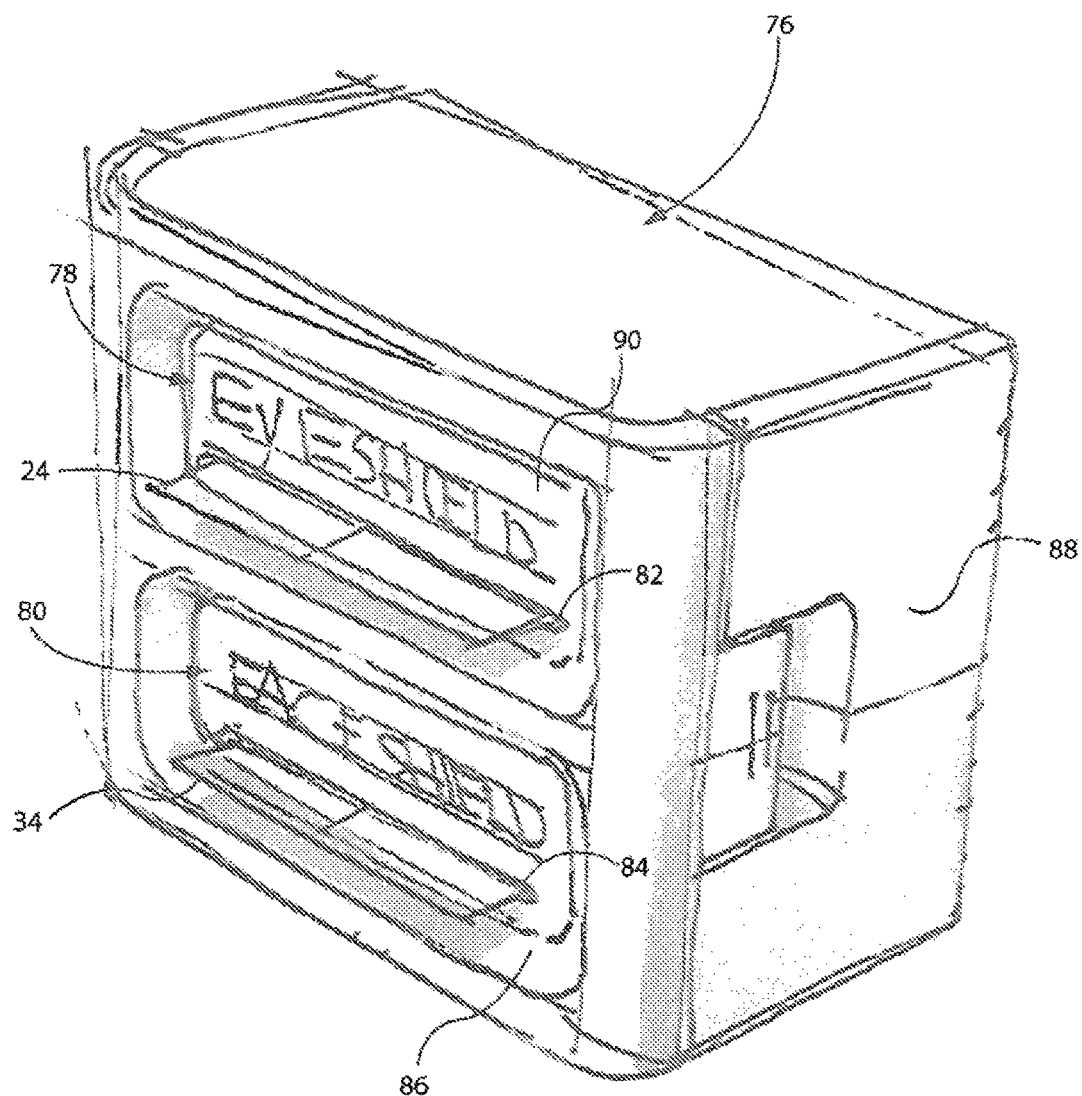
FIG. 8 illustrates a dispenser for modular eye protection according to another embodiment of the invention.

Now turning to FIG. 8, an alternative dispenser 76 may be used to dispense lenses 22 as shown in any of the previous figures. The dispenser 76 preferably includes an eye shield lens-dispensing portion 78 that is attached to the face shield lens-dispensing portion 80. The two dispensing portions 78, 80 may be attached together allowing for a common access panel 88 to access the interior of the dispenser 76, the face shield lens storage compartment 86, and eye shield lens storage compartment 90, which may be useful for restocking the dispenser 76. The dispenser 76 may also include a first opening 82 on the eye shield lens-dispensing portion 78 through which eye shield lenses 24 may be dispensed. The dispenser 76 may also include a second opening 84 on the face shield lens-dispensing portion 80 through which face shield lenses 34 may be dispensed. The dispenser 76 may also include additional dispensing portions for dispensing any device shown in any of the figures.

Figure 9A:
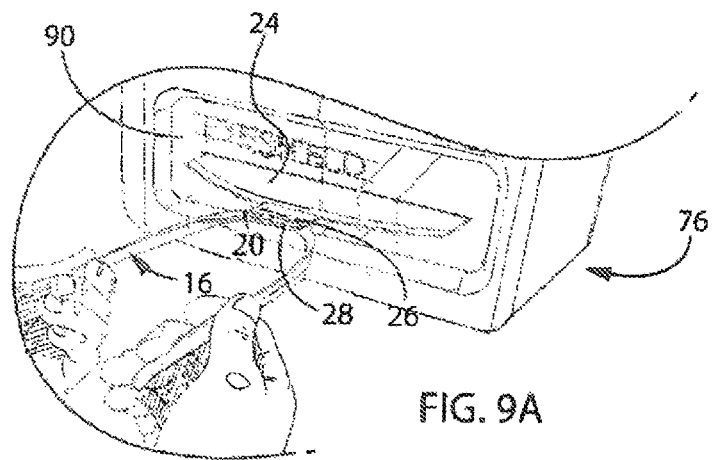
FIG. 9A illustrates a partial perspective view of the operation of the dispenser of FIG. 8.
Figure 9B:
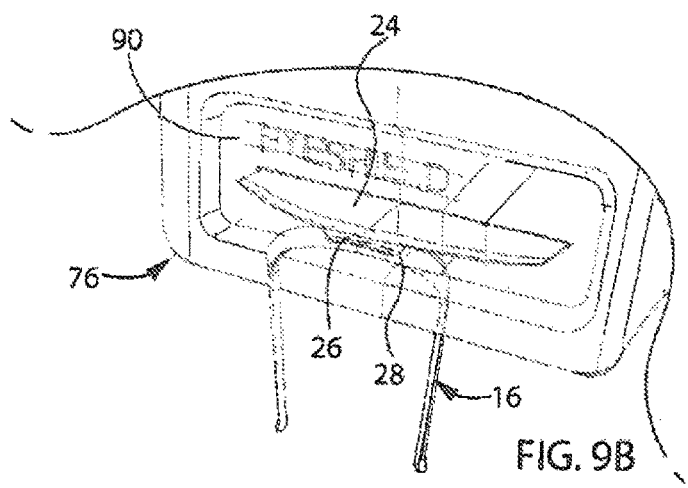
FIG. 9B illustrates a partial perspective view of the operation of the dispenser of FIG. 8.
Figure 9C:
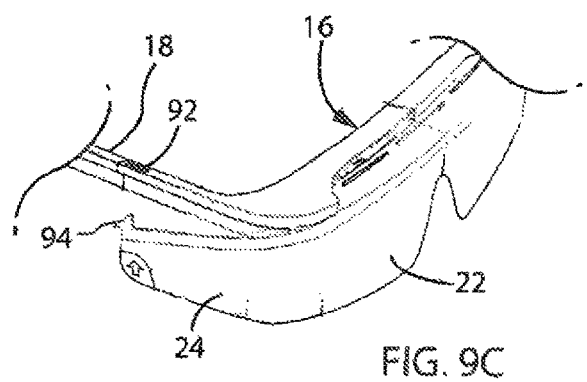
FIG. 9C illustrates a partial perspective view of the modular eye protection assembled in FIGS. 9A-9B.

FIGS. 9A, 9B, and 9C illustrate how the dispenser 76 may be used. Beginning with FIG. 9A, a frame 16 is positioned in front of the eye shield lens-dispensing portion 90 such that the female component 28 of the eye shield lens 24 may be positioned over the central portion of the top bar 20. The frame 16 may then be pivoted in a downward direction to approximately 90° with respect to the eye shield lens 24. This allows the male component 26 of the frame to interact with the female component 28 of the eye shield lens 24. The frame 26 may be slightly pushed against the eye shield lens 24 allowing for proper interference fit of the female component 28 and the male component 26. The frame 16 may then be drawn away from the eye shield lens-dispensing portion 90 that will draw the eye shield lens 24 out of the eye shield lens-dispensing portion 90. At this point, the eye shield lens 24 may be slightly curved to match the profile of the frame 16. A push to connect attachment 94 on the ends of the eye shield lens 24 may then be inserted into a receiving hole 92 and each temple 18 of the frame 16. Due to the shape of the push to connect attachment 94, the eye shield lens 24 is effectively fastened to the frame 16. The attachment of a lens 22 to the frame 16 using a receiving hole 92 on the frame 16 and a push to connect attachment 94 on the ends of the lens 22 may be used in any of the modular eye protection embodiments. In addition, the push to connect attachment 94 may be in the form of any suitable attachment device such as a male post being inserted into a receiving hole with an interference fit or even hook and loop fasteners. Preferably, the attachment means of the lens 22 to a frame 16 does not require any additional fasteners and the fastening means are incorporated on the frame 16 and respective lens 22.

Figure 10A:
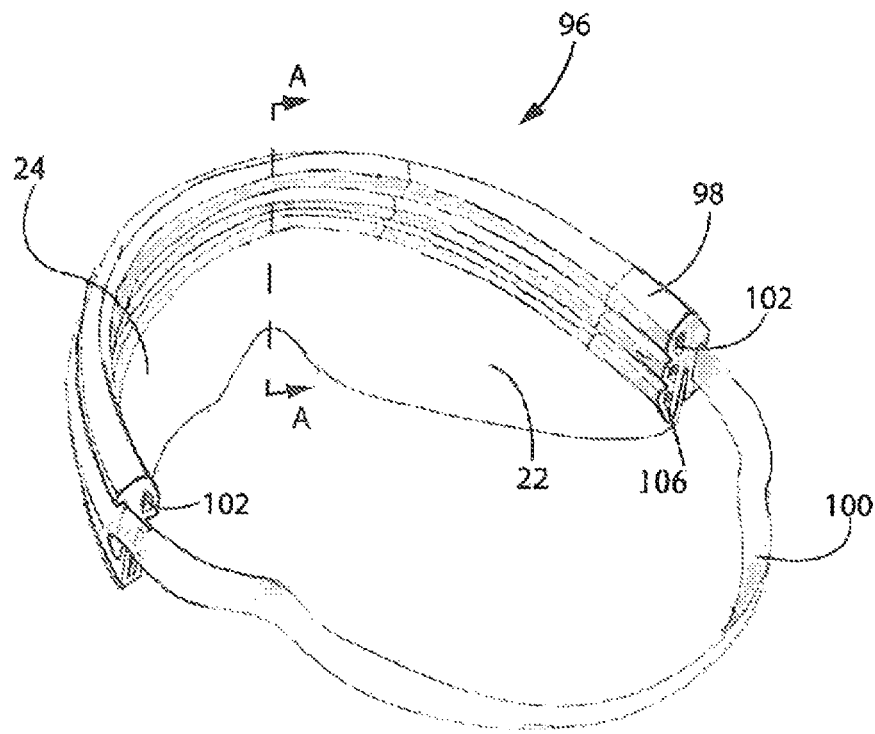
FIG. 10A illustrates a perspective view of modular eye protection according to another embodiment of the invention.
Figure 10B:
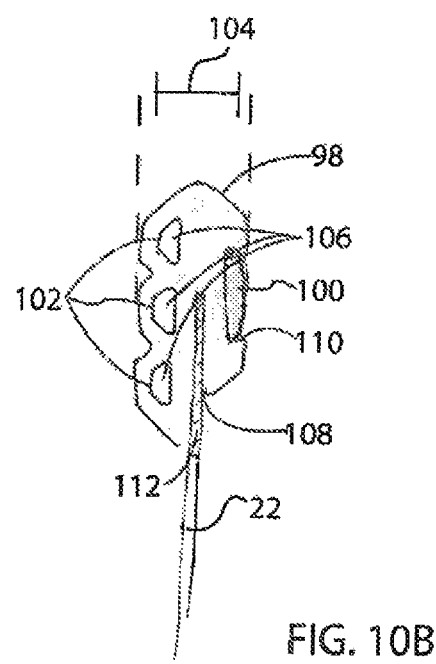
FIG. 10B illustrates a section view along line AA of FIG. 10A.

An alternative embodiment of modular eye protection 14 is shown in FIGS. 10A and 10B. In this embodiment, a modular headband 96 includes a forehead pad 98 and an elastic band 100. The forehead pad 98 is constructed out of any suitable material such as rubber, felt, plastic, paper, and foam. Preferably, the forehead pad 98 is constructed out of a molded polyurethane foam. The polyurethane foam may be open cell or closed cell. The forehead pad 98 may also be extruded or molded in a long length and cut to the desired size during manufacturing. A lens 22 may be inserted into a first reception slot 108 on the forehead pad 98. Preferably, the first reception slot 108 may receive the lens 22 with a simple interference fit. The elastic band 100 may fit in a second reception slot 110 that extends along the length of the forehead pad 98. This configuration allows the forehead pad 98 to conform to various shapes of a person's head with the applied pressure of the elastic band 100. The forehead pad 90 includes openings 106 on each end of the forehead pad 98 for channels 102. The channels 102 extend through the interior of the forehead pad 98, lengthwise, along the forehead pad 98. The channels 102 provide for air flow and increased cushioning when the forehead pad 98 is worn by an individual. Additionally, the thickness 104 of the forehead pad 98 may vary depending on the particular application. For example, a thinner forehead pad 98 may be suitable for a smaller individual while a thicker forehead pad 98 may be preferable for a larger individual. The lens 22 may also include a printed area 112. The printed area 112 may be included in any of the lenses 22 in any of the modular eye protection 14 embodiments shown in any of the figures. The printed area 112 assists in reducing glare from light sources in front of the lens 22. The printed area preferably only covers an upper portion of the lens 22, including a small portion of the lens 22 that extends out of the second reception slot 110.

Figure 11A:
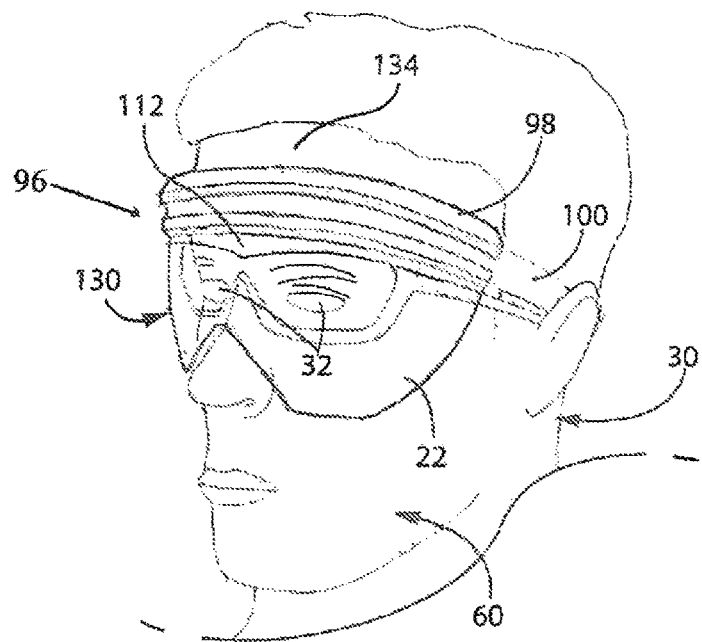
FIG. 11A illustrates a perspective view of the modular eye protection of FIG. 10A being worn by a person.
Figure 11B:
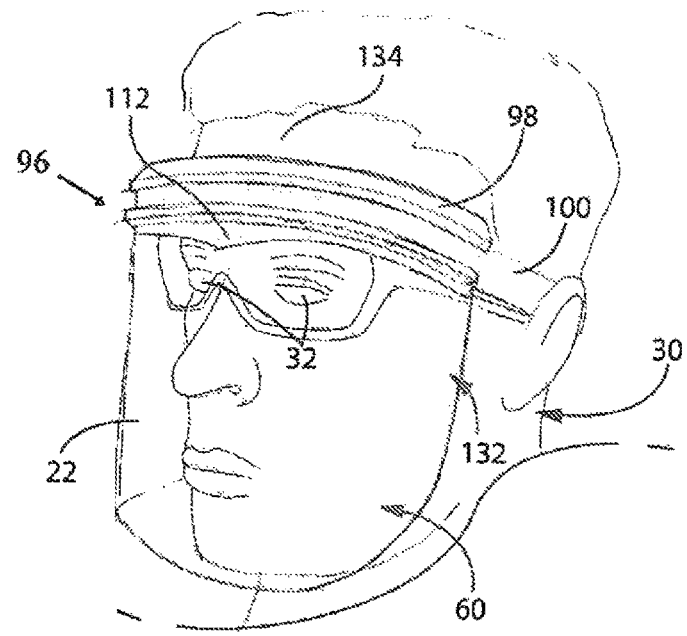
FIG. 11B illustrates a perspective view of a modular eye protection according to another embodiment of the invention being worn by a person.

FIGS. 11A and 11B show modular eye protection 14 in different embodiments of the modular headband 96 variant as disclosed above. FIG. 1A shows one embodiment in which the lens 22 of the forehead pad 98 is an eye shield lens 130. The elastic band 100 surrounds the wearer's head allowing the forehead pad 98 to conform to the forehead 134 of the person 30. The eye shield lens 130 protects the eyes 32 of the person 30. The eye shield lens 130 may also extend down a portion of the face 60. The printed area 112 is shown to only include a small portion of the eye shield lens 130. FIG. 1B shows another embodiment in which the lens 22 is a face shield lens 132. The face shield lens 132 protects the eyes 32 and also covers the entire portion of the face 60 that is below the forehead pad 98.

Figure 12A:
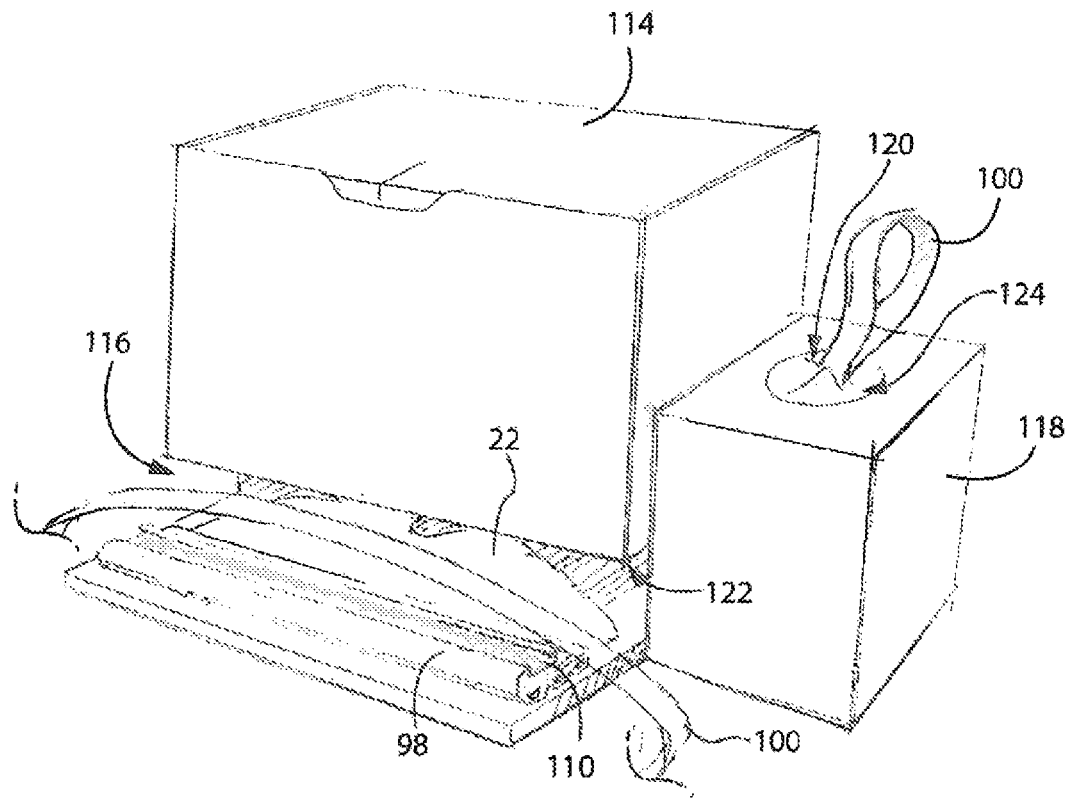
FIG. 12A illustrates a perspective view of a dispenser for the modular eye protection of FIG. 10A.
Figure 12B:
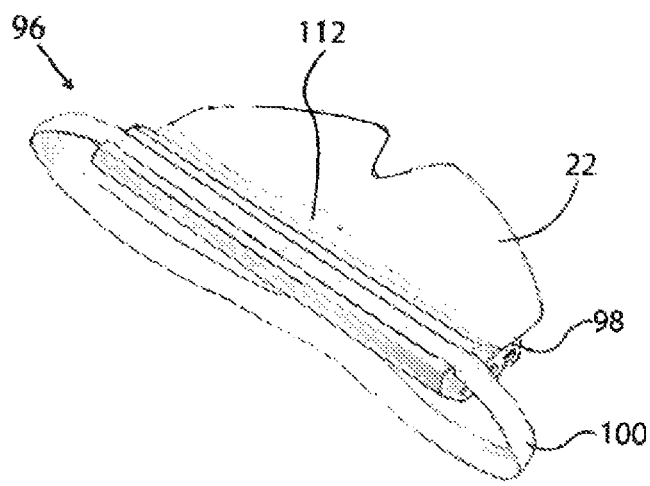
FIG. 12B illustrates a perspective view of modular eye protection according to another embodiment of the invention.

Turning now to FIG. 12A, a first storage vessel 114 is shown that dispenses forehead pads 98 that are already attached to a lens 22. The lens 22 may be either a face shield lens 132 or an eye shield lens 130. The first storage vessel 114 includes a first opening 116 through which the forehead pad 98 and attached lens 22 may be dispensed. The first storage vessel 114 may be in the form of a box that has a first cavity 122 in which forehead pads 98 and attached lenses 22 may be stored. A panel that opens to allow proper refilling may be further included, or the box may be disposable. Additionally, any device may be dispensed from the first storage vessel 114 such as just forehead pads 98, just lenses 22, or fully-assembled modular headbands 96. A second storage vessel 118 may be located alongside the first storage vessel 114. The second storage vessel 118 may include a second cavity 124 that stores a plurality of elastic bands 100. Each individual elastic band 100 may be connected to another elastic band 100 similar to tissues in a tissue box. As an elastic band 100 is drawn out of a second opening 120, an additional elastic band 100 may be exposed from the second opening 120. The first elastic band 100 may then detach from the other elastic band 100 much like drawing a tissue from a tissue box. FIG. 12B shows a representation of an assembled modular headband 96 including a forehead pad 98 attached to an elastic band 100 and a lens 22. The printed area 112 may also be seen.

Figure 13:
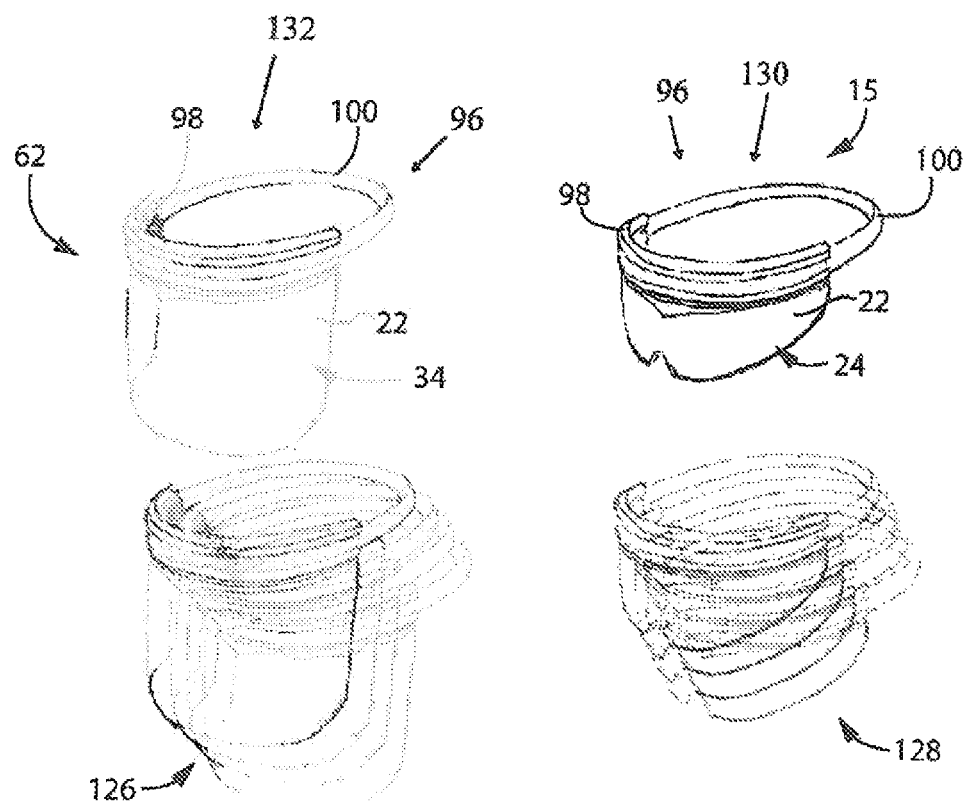
FIG. 13 illustrates a perspective view of storage and packing options of modular eye protection.

Turning now to FIG. 13, various storage methods for modular eye protection, in this case modular head bands 96, are shown. Forehead pads 98 may be attached to elastic bands 100 and lenses 22 to form face shields 62 or eye shields 15, as described above. Due to the shape of the modular head bands 96, vertically stacked face shields 126 or vertically stacked eye shields 128 may be assembled allowing for compact storage and transportation. The vertically stacked face shields 126 and vertically stacked eye shields 128 may also be assigned stock keeping unit numbers "SKUs" designating which dispenser, or department the devices are intended for. The SKU may also define any desired information that is intended to be communicated.

The individual components need not be formed in the disclosed shapes, or assembled in the disclosed configuration, but could be provided in virtually any shape and assembled in virtually any configuration. Further, although various embodiments of eye protection, face shields, head bands, and dispensers are described herein with certain features, any of the features may be combined with or removed from any of the embodiments. Furthermore, all the disclosed features of each dispenser may be combined with, or substituted for, the disclosed features of every other embodiment.

It is intended that the appended claims cover all such additions, modifications and rearrangements. Expedient embodiments of the present invention are differentiated by the appended claims.

What is claimed is:

1. A modular eye protection comprising:
a frame including temples and a top bar;
a detachable nose bridge configured to attach to the lens with an interference fit;
a lens configured to attach to the frame, with a male and a female component that are retained together with an interference fit;
wherein the modular eye protection is configured to be disposable following a single use;
a dispenser configured to dispense the frame, the detachable nose bridge, and the lens, the dispenser comprising:
a frame dispensing portion including a vertical, unobstructed dispensing column with a dispensing opening at a bottom portion of the column, configured to receive a cartridge of a plurality of frames and dispense a single frame at a time;
an access panel configured to open and communicate with the dispensing column of the frame dispensing portion;
a lens dispensing portion attached to the frame dispensing portion including an eye shield lens dispensing portion and a face shield lens dispensing portion;
the face shield lens dispensing portion including a storage compartment configured to store a plurality of face shields lenses, and a slider configured to advance a new face shield lens while minimizing a user's hands from contacting the new face shield lens following a dispensing of a face shield lens;
the eye shield lens dispensing portion including a storage compartment configured to store a plurality of eye shield lenses, and a slider configured to advance a new eye shield lens while minimizing the user's hands from contacting the new eye shield lens following a dispensing of an eye shield lens; and
an access panel configured to open and communicate with the storage compartments of the eye shield lens dispensing portion and the face shield lens dispensing portion.

2. The modular eye protection of claim 1 wherein the dispenser further includes a bagged dispensing portion connected to the lens dispensing portion configured to dispense one of a plurality of an individually bagged eye shield lenses, and an individually bagged face shield lens, and a mask.

3. The modular eye protection of claim 1, further comprising:
a hinged panel on a side of the face shield lens dispensing portion and the eye shield lens dispensing portion allowing access to a cavity within the face shield lens dispensing portion and access to a cavity within the eye shield lens dispensing portion.

4. The modular eye protection of claim 1, further comprising a common access panel that covers up an interior of the face shield lens dispensing portion and the eye shield lens dispensing portion.

5. The modular eye protection of claim 1, further comprising:
a first access panel associated with the face shield lens dispensing portion;
a second access panel associated with the eye shield lens dispensing portion;
wherein the first access panel allows for access of the face shield lens dispensing portion; and
wherein the second access panel allows for access of the face shield lens dispensing portion.

6. The modular eye protection of claim 1, wherein the column is configured to allow gravity to power the delivery of a plurality of frames to the dispensing opening.

7. The modular eye protection of claim 1,
wherein the access panel is removable to allow for access to an interior of the column.

8. The modular eye protection of claim 1, further comprising:
an opening in the eye shield lens dispensing portion that is located adjacent to a bottom of the eye shield lens dispensing portion; and
an opening in the face shield lens dispensing portion that is located adjacent to a bottom of the face shield lens dispensing portion.

9. The modular eye protection of claim 8, wherein gravity feeds the eye shield lens to the opening in the eye shield lens dispensing portion; and
wherein gravity feeds the face shield lens to the opening in the face shield lens dispensing portion.

10. The modular eye protection of claim 3, further comprising:
a mask dispensing compartment connected to the face shield lens dispensing portion and the eye shield lens dispensing portion; and
an opening in the mask dispensing compartment configured to dispense a single mask at a time; wherein
the hinged panel on the side of the face shield lens dispensing portion and the eye shield lens dispensing portion allows access to a cavity within the mask dispensing compartment configured to store a plurality of masks.

* * * * *